United States Patent [19]

Smith, III

[11] Patent Number: 4,817,604

[45] Date of Patent: Apr. 4, 1989

[54] DISPOSABLE CHOLANGIOGRAM CLIP

[76] Inventor: Ray C. Smith, III, 7544 Iron Horse La., Indianapolis, Ind. 46256

[21] Appl. No.: 95,120

[22] Filed: Sep. 11, 1987

[51] Int. Cl.$^4$ ............................................. A61B 17/00
[52] U.S. Cl. ..................................... 128/346; 604/174
[58] Field of Search ............... 128/321, 325, 326, 346; 604/174

[56] References Cited

U.S. PATENT DOCUMENTS

| | | | |
|---|---|---|---|
| 3,013,560 | 12/1961 | Cohen | 128/346 |
| 3,509,882 | 5/1970 | Blake | 128/325 |
| 4,458,681 | 7/1984 | Hopkins | 128/346 |
| 4,484,911 | 11/1984 | Berlin et al. | 128/346 |
| 4,498,903 | 2/1985 | Mathew | 604/174 |
| 4,558,699 | 12/1985 | Bashour | 128/346 |
| 4,671,282 | 6/1987 | Tretbar | 128/321 |
| 4,733,666 | 3/1988 | Mercer, Jr. | 128/346 |

OTHER PUBLICATIONS

Banich, F., Simple Rapid Method of Securing a Cystic Duct Catheter, Surgery, Gynecology & Obstetrics, 155:557,558; Oct. 1982.
Hampson, L., Hreno, A., A Simple Method for Catheter Fixation of the Duct During Cholangiography, Surgery, Gynecology & Obstetrics, 59:83; Jul. 1984.
Hopkins, N., Powis, S., Method of Cannula Fixation for Operative Cholangiography, British Journal of Surgery, 72:846; Oct. 1985.
Keiller, F., Operative Cholangiography, British Journal of Surgery, 72:846; Oct., 1985.
White, T., Hart, M., Cholangiography and Small Duct Injury, The American Journal of Surgery, 149:640; May, 1985.
American V. Mueller 1981 advertising brochure entitled "The Taufic Cholangioclamp".

Primary Examiner—John D. Yasko
Attorney, Agent, or Firm—Woodard, Emhardt, Naughton, Moriarty & McNett

[57] ABSTRACT

A tool and method for transcystic duct operative cholangiography. A clip having a pair of spring biased jaws has an aperture formed on the jaws. The clip is positioned around the cystic duct and a catheter is extended through the aperture. A needle nose shaped clamp is releasably engageable with the clip and forces the jaws apart to extend around the cystic duct. Release of the clamp allows a spring within the clip to force the jaws together sealing the duct and catheter together.

9 Claims, 2 Drawing Sheets

DISPOSABLE CHOLANGIOGRAM CLIP

BACKGROUND OF THE INVENTION

This invention is in the field of surgical instruments and more specifically clips for clamping onto tissue.

In a transcystic duct operative cholangiogram, a catheter is extended into the cystic duct. In order to obtain a seal around the catheter and to anchor the catheter in place, a clamp or ligature is placed around the catheter. Such prior techniques of obtaining a seal around the catheter are described in the following publications:

1. Banich, F., Simple Rapid Method of Securing A Cystic Duct Catheter, Surgery, Gynecology & Obstetrics. 155:557,558; October 1982.
2. Hampson, L., Hreno, A., A Simple Method for Catheter Fixation of The Cystic Duct During Cholangiography, Surgery, Gynecology & Obstetrics. 59:83; July 1984.
3. Hopkins, N., Powis, S., Method of Cannula Fixation for Operative Cholangiography, British Journal of Surgery. 72:427; June 1985.
4. Keiller, F., Operative Cholangiography, British Journal of Surgery. 72:846; October 1985.
5. White, T., Hart, M., Cholangiography And Small Duct Injury, The American Journal of Surgery. 149:640; May 1985.

Cystic duct catheterization may be accomplished by a needle nose clamp having a hole extending through the jaws of the clamp to receive the catheter which in turn is extended into the cystic duct. The jaws are then used to hold the catheter while a sealing ligature is applied about the catheter and the cystic duct. Such a clamp is available from American V. Mueller, division of American Hospital Supply Corporation. Such methods are both frustrating and time consuming. Further, damage to the tissues of the cystic and common ducts can occur particularly when the catheter becomes dislodged. Likewise, a fairly large incision is required to allow the surgeon to correctly position the clamp or a ligature around the catheter. Disclosed herein is a new and improved clip which may be quickly clipped on to the duct with the catheter extending directly through the jaws of the clip ensuring a superior seal while anchoring the catheter in place and particularly limiting the damage to the cystic tissues of the duct. Also disclosed is a new and improved clamping tool to be used with the clip which allows for a shorter incision.

SUMMARY OF THE INVENTION

One embodiment of the present invention is a surgical tool comprising a clamp having a pair of mutually opposed distal ends and a pair of proximal ends releasably lockable to controllably space apart the distal ends, and a tissue clip having a first control end and a second control end lockingly engaged by the distal ends of the clamp, the clip further having a pair of spring biased mutually opposed jaws controllably movable apart by movement of the first control end and the second control end with the jaws being movable from an open position to a closed position, the jaws including an aperture formed thereon through which a catheter may extend when the jaws are clamped onto tissue.

A further embodiment of the present invention is a surgical method of transcystic duct operative cholangiography comprising the steps of surgically opening the cystic duct, inserting a tube into the surgical opening, providing a clip with mutually facing jaw surfaces having an aperture formed on the jaw surfaces, clamping the mutually facing jaw surfaces of the clip onto the cystic duct and around the tube at the surgical opening to seal the cystic duct and tube together, and, performing a cholangiogram through the aperture and the tube.

Yet another embodiment of the present invention is a surgical method of transcystic duct operative cholangiography comprising the steps of surgically removing the gallbladder, inserting a tube into the junction of the cystic duct and the gallbladder, providing a clip with mutually facing jaw surfaces having an aperture formed on the jaw surfaces, clamping the mutually facing jaw surfaces of the clip onto the cystic duct and around the tube at the junction to seal the cystic duct and tube together, and performing a cholangiogram through the aperture and the tube.

It is an object of the present invention to provide a cholangiogram clip for sealingly holding a catheter extending into a duct.

A further object of the present invention is to provide a new and improved surgical method of transcystic duct operative cholangiography.

In addition, it is an object of the present invention to provide a tool and method for use in operative cholangiography which minimize damage to duct tissue and require a shorter incision.

Related objects and advantages of the present invention will be apparent in the following description.

DESCRIPTION OF THE PREFERRED EMBODIMENT

Figure 1:
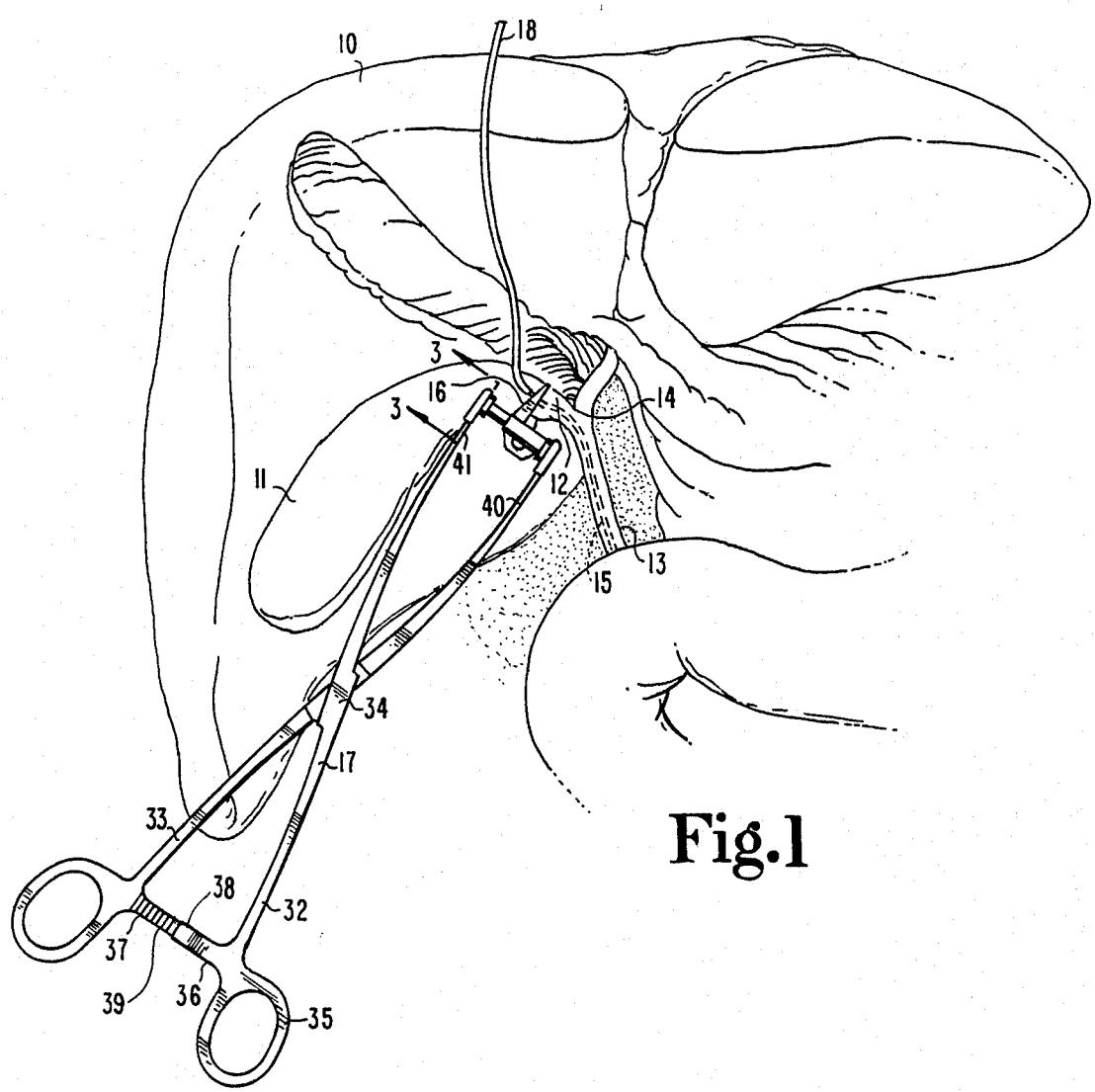
FIG. 1 is a view showing the clamp and clip incorporating the present invention holding a catheter relative in a duct.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now more particularly to FIG. 1, there is shown the patient's liver 10, gallbladder 11, cystic duct 12, the common bile duct 13 and the junction 14 between the common bile duct and cystic duct. My surgical method of transcystic duct operative cholangiography allows for dissection of the gallbladder and cystic duct in the usual manner beginning at the dome of the gallbladder. The loose connective tissue is cleared from the cystic duct 12 and the junction 14 of the cystic duct. The cystic duct 12 is then opened or the gallbladder 11 is removed and the cystic duct is then cannulated with a 5F infant nagogastric tube 15. Such a tube is less rigid and allows for the placement of its opening away from the tube tip preventing the tube from becoming obstructed should it be placed against a cystic duct valve leaflet. My new and improved clip 16 is then applied with my new and improved clamp 17. The cholangiogram is then performed via tube 18 aligned with the opening in tube 15. Use of clip 16 ensures minimum damage to the tissue with the clip being easily removed and reapplied if a second cholangiogram is needed. The length of the jaws of the clip provides a good seal where bulky tissue is present or if a cystic duct is cannulated through a transected infundibulum.

Figure 2:
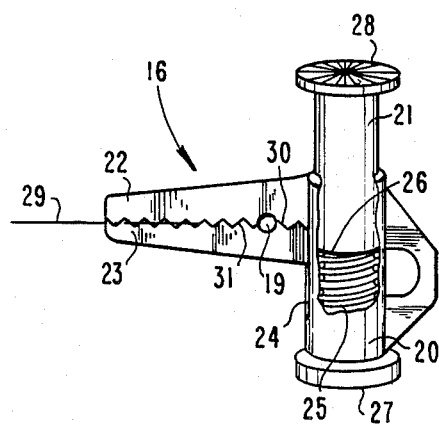
FIG. 2 is an enlarged fragmentary view of the clip depicted in FIG. 1.

Clip 16 is identical with commercially available surgical clips with the exception that my clip includes an aperture or hole 19 (FIG. 2) formed on the mutually facing surfaces of the clip jaws thereby enabling tube 15 to be extended through the jaws while the jaws are simultaneously clamped onto tissue. Clip 16 includes a tubular main body 20 into which is slidable a rod-shaped second body 21. A first jaw 22 is integrally attached to hollow main body 20 whereas a second jaw 23 is integrally attached to the rod-shaped second body 21. Jaw 23 extends through a slot 24 formed in main body 20 with the slot extending along the longitudinal axis of body 20 allowing jaw 23 to slide to and from jaw 22. Main body 20 is fragmented to illustrate the positioning of a helical spring 25 which forces the bottom end 26 of body 21 upwardly relative to body 20 thereby forcing jaws 22 and 23 together. A pair of disc shaped ends 27 and 28 are integrally mounted to the opposite ends of body 20 and body 21 with each end 27 and 28 including a plurality of radially extending ridges formed thereon. Movement of end 28 toward end 27 results in jaws 22 and 23 opening whereas release of ends 27 and 28 causes the helical spring to move the jaws together. Hole 19 extends perpendicularly across the longitudinal axis 29 of jaws 22 and 23. The hole is formed by a semi-circular recess formed on jaw surface 30 and an aligned semi-circular recess formed on jaw surface 31. The semi-circular recess as formed on the mutually facing and contacting surfaces of jaws 22 and 23 thereby form hole 19 which extends completely across the jaws. Likewise, the mutually facing surfaces of jaws 22 and 23 may be provided with a plurality of ridges or teeth for gripping the tissue upon which the jaws are closed.

Figure 3:
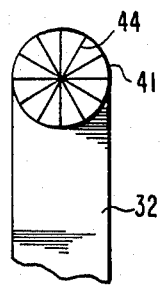
FIG. 3 is an enlarged fragmentary cross-sectional view taken along a line of FIG. 1 and viewed in the direction of the arrows 3—3.

Clamp 17 is identical with prior art clamps with the exception of the size and shape of the clamp main body and with the further exception of the distal end means for engaging the clip. Clamp 17 includes a pair of rigid elongated members 32 and 33 pivotally mounted together at an intermediate position 34 between the distal and proximal ends. Finger holes 35 are formed at the proximal ends of each member. Locking means is provided adjacent the finger holes to allow the clamp to lockingly engage and hold clip 16. The locking means includes a pair of inwardly extending ribs 36 and 37 having outer ends integrally secured respectively to members 32 and 33 with the inner end 38 of rib 36 being releasably engageable with the inner end 39 of rib 37. A plurality of interlocking ribs are provided on the mutually facing inner ends 38 and 39 of the ribs. The distal ends 40 and 41 of members 32 and 33 have mutually facing surfaces releasably engageable with control ends 27 and 28 of clip 16. Proximal disc shaped ends 40 and 41 include a plurality of radially extending ridges 44 (FIG. 3) complementary in shape to the radially extending ribs on ends 27 and 28. Thus, proximal ends 40 and 41 matingly receive ends 27 and 28 and securely hold the clip. Initially, finger holes 35 may be moved together by forcing proximal ends 40 and 41 against ends 27 and 28 depressing bodies 20 and 21 and thereby moving the jaws 22 and 23 apart to extend around the duct. The finger holes may then be moved apart thereby releasing spring 25 and allowing the jaws to come together securely clamping the duct. Ribs 36 and 37 then secure the finger holes apart the desired distance.

Figure 4:
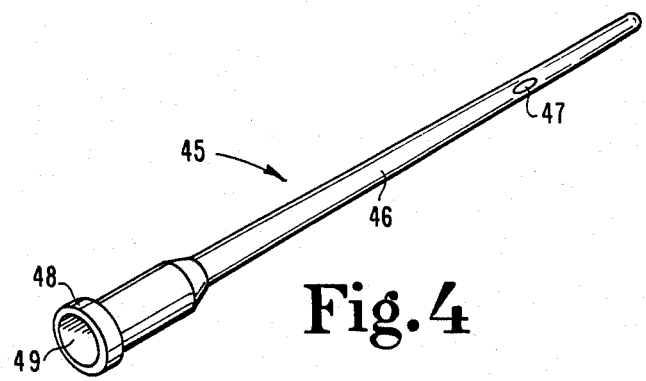
FIG. 4 is a perspective view of a catheter.
Figure 5:
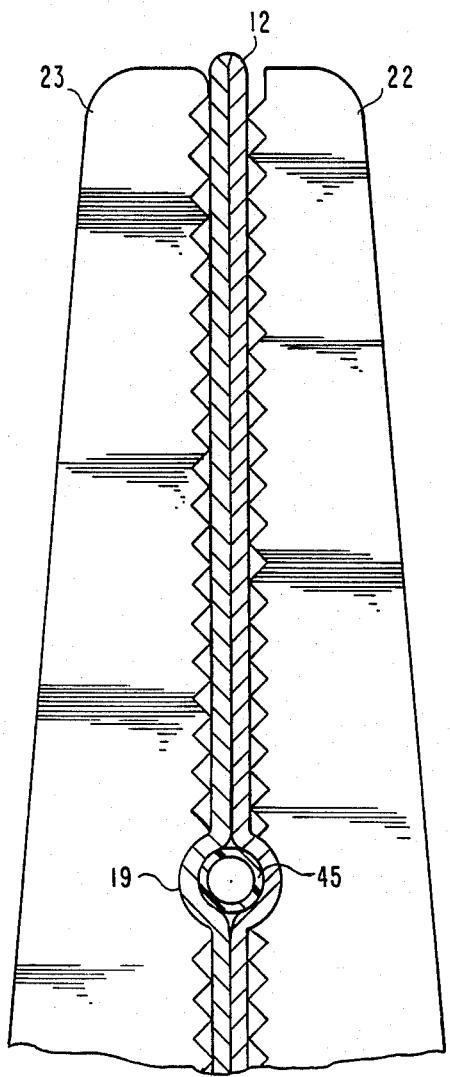
FIG. 5 is a fragmentary enlarged view of the jaws of the clip.

In lieu of inserting tube 15 into the duct, a conventional catheter 45 (FIG. 4) may be inserted into the duct opening. The clamp jaws 22 and 23 (FIG. 5) are then extended around the cystic duct and main body 46 of catheter 45 with the catheter main body being extended through aperture 19 of the clip jaws. The jaws are then closed forcing duct 12 around and against the catheter not only holding the catheter in place but also achieving a seal between the duct and catheter. In the event tube 15 is used in lieu of catheter 45, then the tube is inserted through the duct aperture and the jaws of the clip are clamped onto the tube and cystic duct in an identical manner.

The outer end 48 of catheter 45 is positioned externally of the cystic duct and is utilized for performing the cholangiogram through opening 49. A second opening 47 located at the opposite end portion of the catheter allows the fluid to flow through the catheter and into the cystic duct. In an identical manner, tube 15 includes an end located outwardly of the cystic duct and has an outer aperture to receive the cholangiogram tube 18. The opposite end of tube 15 located within the duct includes an aperture allowing the cholangiogram fluid to flow through tube 15 and into the duct.

The size and configuration of clamp 17 allows for a smaller incision as compared to the incision required for prior clamps. Clamp 17 has a minimum overall length from the proximal to distal ends of at least 26 cm enabling the surgeon to extend the clamp and clip into the wound to the cystic duct. By utilizing my clip and clamp, the length of the incision is approximately only 4 to 6 cm in length. The clip applicator or clamp 17 must be able to apply and release clip 16 within the length of the incision. The width of clip 17 measured at the proximal end of the clamp or from the outside of one finger hole 35 to the outside edge of the opposite finger hole is 26 mm when the clamp is closed and jaws 22 and 23 are in the open position whereas the same distance is 38 mm when the clamp is open and the jaws 22 and 23 are in the closed condition. A 10° bend in members 32 and 33 is provided adjacent finger holes 35.

Many variations are contemplated and included in the present invention. For example, the clamp may be produced from metal or plastic. Likewise, the clip may be produced from a radiopaque plastic.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:
1. A surgical tool comprising;
   a clamp having a pair of mutually opposed distal ends and a pair of proximal ends releasably lockable to controllably space apart said distal ends;

a tissue clip having a first control end and a second control end lockingly but removably engagable with said distal ends of said clamp, said clip further having a pair of spring biased mutually opposed jaws controllably movable apart by movement of said first control end and said second control end with said jaws being movable from a open position to a closed position, at least one of said jaws including an aperture formed thereon through which a body tube may extend when said jaws are clamped onto tissue; and, a catheter insertable through said aperture when said jaws are clamped onto tissue sealing same to said catheter and allowing fluid flow through said catheter while said clip is positioned thereon.

2. The surgical tool of claim 1 wherein:
said jaws have mutually facing surfaces with said aperture formed on said surfaces and extending thereacross.

3. The surgical tool of claim 2 wherein:
said jaws are elongated in a first direction with said aperture extending perpendicular to said first direction.

4. The surgical tool of claim 3 wherein:
said clip includes a hollow main body integrally attached to said first control end and to one of said jaws and further includes a rod shaped main body slidably mounted to said hollow main body and attached to said second control end and to the other of said jaws, said clip includes a spring positioned within said hollow main body between said first control end and said rod shaped main body and urging said jaws together but yieldable to allow said jaws to move apart when said first control end is moved toward said second control end as said distal ends of said clamp are moved together; and,
said distal ends of said clamps include mutual facing disc shaped surfaces with a plurality of ridges formed thereon to lockingly receive complementary shaped surfaces formed on said first control end and said second control end of said clip.

5. A surgical tool for use in a transcystic duct operative cholangiogram comprising:
a clamp having a pair of mutually opposed distal ends and a pair of proximal ends releasably lockable to controllably space apart said distal ends;
a cystic duct clip having a first control end and a second control end lockingly but removably engagable with said distal ends of said clamp, said clip further having a pair of spring biased mutually opposed jaws controllably movable together when said cystic duct is located therebetween by movement of said first control end and said second control end, at least one of said jaws including an aperture formed thereon; and, a cholangiogram catheter extendable through said aperture into said cystic duct when said jaws are clamped onto said cystic duct.

6. The surgical tool of claim 5 wherein:
said clip includes a hollow main body integrally attached to said first control end and to one of said jaws and further includes a rod shaped main body slidably mounted to said hollow main body and attached to said second control end and to the other of said jaws, said clip includes a spring positioned within said hollow main body between said first control end and said rod shaped main body and urging said jaws together but yieldable to allow said jaws to move apart when said first control end is moved toward said second control end as said distal ends of said clamps are moved together; and,
said distal ends of said clamp include mutual facing disc shaped surfaces with a plurality of ridges formed thereon to lockingly receive complementary shaped surfaces formed on said first control end and said second control end of said clip.

7. The surgical tool of claim 5 wherein:
said clamp has an minimum overall length of at least 26 centimeters to extend out of the wound.

8. A surgical method of transcystic duct operative cholangiography comprising the steps of:
surgically opening the cystic duct;
inserting a tube into the surgical opening;
providing a clip with mutually facing jaw surfaces at least one of which having an aperture formed thereon;
providing a clamp operatively engagable with said clip;
removably engaging said clamp with said clip;
moving said jaw surfaces apart by moving said clamp;
clamping said mutually facing jaw surfaces of said clip onto said cystic duct and around said tube at the surgical opening sealing said duct and said tube together; and,
performing a cholangiogram through said aperture and said tube while said clip remains therein.

9. A surgical method of transcystic duct operative cholangiography comprising the steps of:
surgically removing the gallbladder;
inserting a tube into the junction of the cystic duct and the gallbladder;
providing a clip with mutually facing jaw surfaces having an aperture formed on said jaw surfaces;
providing a clamp operatively engagable with said clip;
removably engaging said clamp with said clip;
moving said jaw surfaces apart by moving said clamp;
clamping said mutually facing jaw surfaces of said clip into said cystic duct and around said tube at the junction sealing said duct and said tube together;
removing said clamp; and,
performing a cholangiogram through said aperture and said tube while said clip remains therein.

* * * * *